(12) United States Patent
Miedema et al.

(10) Patent No.: US 12,303,384 B2
(45) Date of Patent: May 20, 2025

(54) ELECTROSPUN HEART VALVES

(71) Applicant: Xeltis AG, Zurich (CH)

(72) Inventors: Jurgen Sander Miedema, Mels (CH); Martijn Antonius Johannes Cox, Budel (NL)

(73) Assignee: Xeltis AG, Zurich (CH)

( * ) Notice: Subject to any disclaimer, the term of this patent is extended or adjusted under 35 U.S.C. 154(b) by 386 days.

(21) Appl. No.: 17/618,449

(22) PCT Filed: Jun. 26, 2020

(86) PCT No.: PCT/EP2020/068151
§ 371 (c)(1),
(2) Date: Dec. 11, 2021

(87) PCT Pub. No.: WO2020/260661
PCT Pub. Date: Dec. 30, 2020

(65) Prior Publication Data
US 2022/0346947 A1      Nov. 3, 2022

Related U.S. Application Data

(60) Provisional application No. 62/867,279, filed on Jun. 27, 2019.

(51) Int. Cl.
*A61F 2/24*          (2006.01)

(52) U.S. Cl.
CPC .......... *A61F 2/2415* (2013.01); *A61F 2/2418* (2013.01); *A61F 2210/0004* (2013.01); *A61F 2230/0067* (2013.01)

(58) Field of Classification Search
CPC ........ A61F 2/24; A61F 2/2412; A61F 2/2415; A61F 2/2418; A61F 2230/0067; B21D 22/16; B01D 69/087
(Continued)

(56) References Cited

U.S. PATENT DOCUMENTS

| 8,409,242 B2 | 4/2013 | Clubb |
| 8,945,209 B2 | 2/2015 | Bonyuet |

(Continued)

FOREIGN PATENT DOCUMENTS

| EP | 1864687 | 7/2013 | |
| WO | 2016138416 | 9/2016 | |
| WO | WO-2017047902 A1 * | 3/2017 | ............... A61F 2/24 |

OTHER PUBLICATIONS

WO2017047902A1—Machine Translation (Year: 2017).*
(Continued)

*Primary Examiner* — Yunju Kim
(74) *Attorney, Agent, or Firm* — LUMEN PATENT FIRM

(57) ABSTRACT

Methods and the resulting structures, like valve devices (e.g. heart or vessel) are provided made by electrospinning single shapes on mandrels with complex surface shapes. These single shapes are then shaped into valves with a plurality of leaflets. Three levels of complexity of shapes are described: 1) conical shapes, 2) a combination of conical and cylindrical shapes, and 3) a conical and/or cylindrical shape which has further complexity by one or more three-dimensional shapes. Heart valves resulting from these complex electrospun shaped mandrels have better mobility dynamics compared to heart valves electrospun on solely cylindrical mandrels.

14 Claims, 6 Drawing Sheets

Conical Preforms

Resulting Electrospun Shapes

(58) Field of Classification Search
USPC .......................................................... 264/634
See application file for complete search history.

(56) References Cited

U.S. PATENT DOCUMENTS

| 2007/0269481 | A1* | 11/2007 | Li | ........................... | A61P 17/02 |
| | | | | | 425/174.8 E |
| 2014/0141152 | A1* | 5/2014 | Sostek | .................. | A61F 2/0063 |
| | | | | | 427/2.24 |
| 2016/0296323 | A1 | 10/2016 | Wulfman | | |
| 2017/0340460 | A1 | 11/2017 | Rosen | | |
| 2018/0071087 | A1* | 3/2018 | Badhwar | ............... | A61L 27/507 |

OTHER PUBLICATIONS

Hobson et al. Fabrication of elastomeric scaffolds with curvilinear fibrous structures for heart valve leaflet engineering. J Biomed Mater Res A. Sep. 2015; 103(9): 3101-3106.

* cited by examiner

Conical Preforms

Resulting Electrospun Shapes 21.5 - 24 mm conical 24 mm cylindrical

Conical Preforms

Resulting Electrospun Shapes

ELECTROSPUN HEART VALVES

FIELD OF THE INVENTION

This invention relates to complex shape structures such as heart-valve leaflets using complex preforms for electrospinning these heart-valve leaflets with the purpose to achieve better leaflet mobility.

BACKGROUND OF THE INVENTION

Forms produced by electrospinning are often used in the medical field, in particular for implant materials, tissue repair, drug delivery, wound dressing and medical textile materials. One area of interest is the creation of implant materials like artificial valves or complex vascular grafts.

Artificial valves are usually produced using animal tissue (e.g. pericardium). There are also artificial valves known in the art that do not use animal tissue. The tissue used is produced normally in flat pieces that have to be put together to create a three-dimensional (3D) shape. This is unfavourable since several components have to be produced and hand sewn together. This is very time consuming and labour intensive and therefore costly process, prone to error and deviations.

In one example, the material used could be produced by electrospinning. Hereby, the material for the leaflets is electro-spun separately and removed from the mandrel. Then three leaflets are mounted on the "valve target". Then the valve conduit is electro-spun thereby also assembling the three leaflets and forming a complete valve. This manufacturing process is complex as you need to manufacture first three separate leaflets prior to manufacturing the whole valve. Alternatively, leaflets could be electro-spun in a tubular form. After removing this tube from the target, the tube is sewed to a frame (covered with synthetic fabric or animal tissue) to create a valve out of it.

A problem with prosthetic heart valves is that they are often not closing correctly. Regurgitation occurs when blood flows back through the valve as the leaflets are closing or when blood leaks through the leaflets when they should be completely closed. Valve regurgitation could place a strain on the heart. It can cause the heart to work harder and it may not pump the correct amount of blood.

The present invention addresses at least some of the problems with the objective of developing technology for easier manufacturing and better dynamics of heart valves.

SUMMARY OF THE INVENTION

The present invention provides methods and the resulting structures of these methods like valve devices (e.g. heart or vessel) made by electrospinning single shapes on mandrels with complex surface shapes. These single shapes are then shaped into valves with a plurality of leaflets (e.g. 2 or 3 leaflets). The invention distinguishes three levels of complexity of shapes: 1) conical shapes, 2) a combination of conical and cylindrical shapes, and 3) a conical and/or cylindrical shape which has further complexity by one or more three-dimensional shapes.

First, the invention is a method of electrospinning a heart valve having a plurality of leaflets using a conical shaped mandrel. In this embodiment, the conical shaped mandrel has a diameter ranging from 16 mm to 28 mm, and has a linear slope angle ranging from 1 to 12.5 degrees. A single conically shaped electrospun scaffold is formed by electrospinning polymers onto the conical shaped mandrel. The single conically shaped electrospun scaffold is then shaped into the heart valve with the plurality of leaflets. It is important to note that the single conically shaped electrospun scaffold remains in one single piece while shaping the plurality leaflets. Further, in this embodiment the method is defined by consisting of electrospinning polymers onto the conical shaped mandrel.

Second, the invention is a method of electrospinning a heart valve having a plurality of leaflets using a mandrel with a conical shaped section and a cylindrical shaped section. In this embodiment, the conical shaped section of the mandrel has a diameter ranging from 16 mm to 28 mm, and the conical shaped section of the mandrel has a linear slope angle ranging from 1 to 12.5 degrees. A single cylindrical and conical shaped electrospun scaffold is formed by electrospinning polymers onto both the conical shaped section and the cylindrical shaped section of the mandrel. The single cylindrical and conical shaped electrospun scaffold is shaped into the heart valve with the plurality of leaflets. It is important to note that the single cylindrical and conical shaped electrospun scaffold remains in one single piece while shaping the plurality leaflets. Further, in this embodiment the method is defined by consisting of electrospinning polymers onto both the conical shaped section and the cylindrical shaped section of the mandrel.

Third, the invention is a method of electrospinning a heart valve having a plurality of leaflets using a complex shaped mandrel with a complex surface. The complex shaped mandrel distinguishes a cylindrical shaped portion, a conical shaped portion, or a combination thereof, and the complex surface further has one or more three-dimensional shapes. In this embodiment, the conical shaped portion of the mandrel has a diameter ranging from 16 mm to 28 mm, the conical shaped portion of the mandrel has a linear slope angle ranging from 1 to 12.5 degrees, and the cylindrical shaped portion has a diameter ranging from 16 mm to 28 mm. A single complex shaped electrospun scaffold is formed by electrospinning polymers onto the complex shaped mandrel including the one or more three-dimensional shapes. The one or more three-dimensional shapes could be one or more bulges to create one or more local bulges in the plurality of leaflets, and/or could be one or more lobes to create one or more local lobes in the plurality of leaflets. The single complex shaped electrospun scaffold is shaped into the heart valve with the plurality of leaflets. It is important to note that the single complex shaped electrospun scaffold remains in one single piece while shaping the plurality leaflets. Further, in this embodiment the method defined by consisting of electrospinning polymers onto the complex shaped mandrel.

In general, for any of these methods and devices, in one embodiment, the polymers are bioabsorbable polymers or biodegradable polymers, which upon implantation could be replaced by new autologous tissue (endogenous tissue restoration (ETR)). In another embodiment, the polymers could also be non-bioabsorbable, i.e. non-degradable.

The objective of these methods and the resulting devices is to develop better geometry, as opposed to fiber alignment, to ensure better opening, closing and stress distribution in the leaflets compared to, for example, heart valves designed from pure cylindrical mandrels. A further objective is to increase/optimize leaflet surface area and/or to define leaflet three-dimensional shape after forming, to optimize/homogenize stress distribution during opening and closing of the leaflets.

In comparison to a cylindrical shape, a conical shape, i.e. smaller diameter at the free edge, will have smaller leaflet with less coaptation plane, which may be beneficial for reducing leaflet redundancy/pinwheeling (see e.g. FIGS. 2-3).

In comparison to a cylindrical shape, an inverse conical shape (larger diameter at the free edge) will have larger leaflets with more coaptation plane, which may be beneficial in case better load distribution through increased coaptation plane is needed.

Complex shapes as taught in this invention, or even further complex shapes, can be used to tune the valve and leaflet geometry as a function of height, allowing more precise tuning of leaflet opening and closing behavior. For example, leaflet opening and closing can be further optimized or improved by minimizing the second moment of area (aka the area of moment of inertia) along the valve height of the leaflet, especially towards the free-end of the leaflet.

DETAILED DESCRIPTION

In this invention, a valve design is proposed with a dedicated 3D shape that improves the closing of the leaflets—in terms of complete closing and correct closing with improved mobility characteristics. In addition, the embodiments producing the 3D shape directly provides advantages in manufacturing compared to building the valves from several flat pieces or other multiple components.

Figure 1:
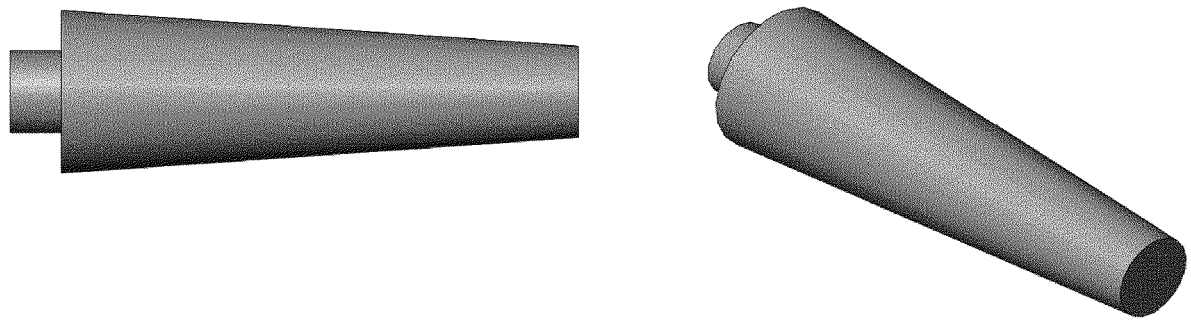
FIG. 1 shows according to an exemplary embodiment of the invention a conical shaped mandrel (top) for forming a single conically shaped electrospun scaffold (middle) by electrospinning polymers onto the conical shaped mandrel (top). It is noted that the single conically shaped electrospun scaffold remains in one single piece after the plurality leaflets have been shaped.
Figure 1:
Figure 2:
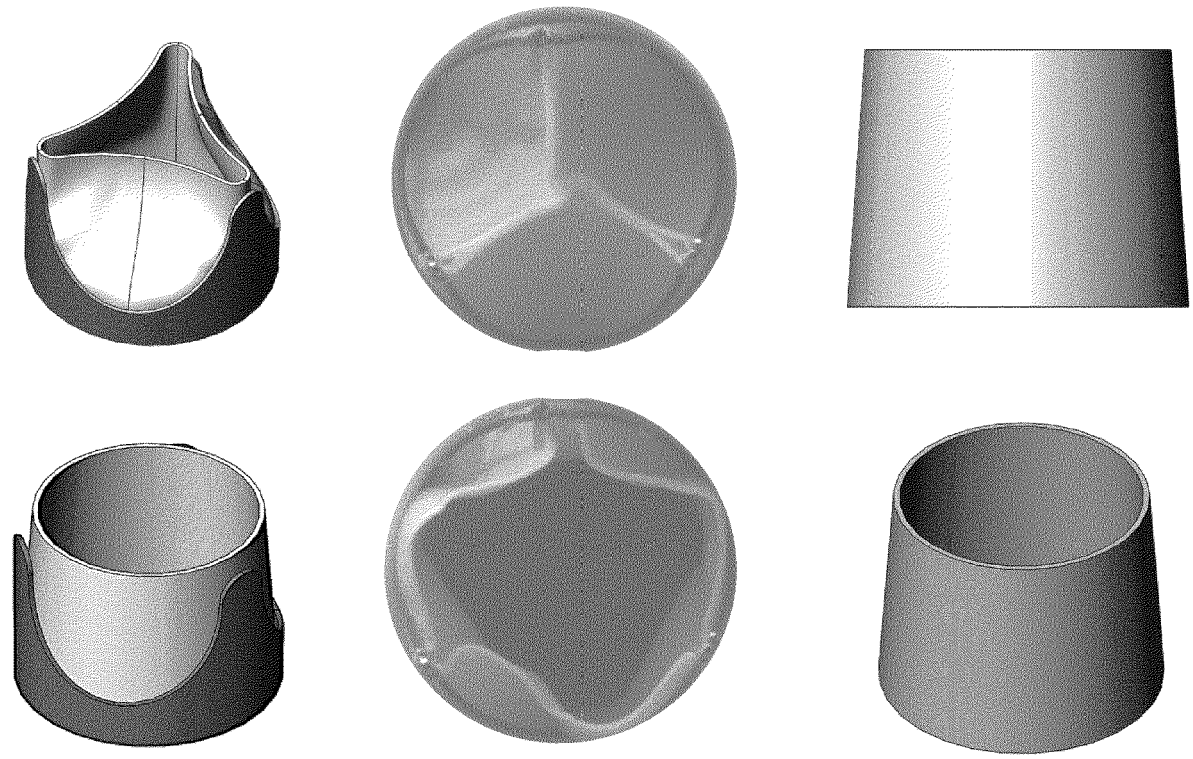
FIG. 2 shows according to an exemplary embodiment of the invention a single conically shaped electrospun scaffold (right column) by electrospinning polymers onto the conical shaped mandrel (FIG. 1). In the left column, a single sheet conically shaped electrospun scaffold is shown (bottom) and a shaped heart valve (top) shaped with the plurality of leaflets is shown based on the single conically shaped electrospun scaffold. It is noted that the single conically shaped electrospun scaffold remains in one single piece while the plurality leaflets have been shaped. In the middle column, the opening (bottom) and closing (top) of this specifically designed heart valve is shown. In comparison to a similar set of images in FIG. 3 for a heart valve made from a single cylindrical shape, better closing and opening dynamics is shown for the heart valve made from a single conical shape.
Figure 3:
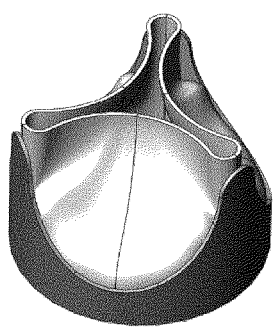
FIG. 3 shows according to an exemplary embodiment of the invention a single cylindrical shaped electrospun scaffold (right column) by electrospinning polymers onto the cylindrical shaped mandrel (FIG. 1). In the left column, a single sheet cylindrically shaped electrospun scaffold is shown (bottom) and a shaped heart valve (top) shaped with the plurality of leaflets is shown based on the single cylindrically shaped electrospun scaffold. It is noted that the single cylindrically shaped electrospun scaffold remains in one single piece while the plurality leaflets have been shaped. In the middle column, the opening (bottom) and closing (top) of this specifically designed heart valve is shown. In comparison to a similar set of images in FIG. 2 for a heart valve made from a single conical shape, worse closing and opening dynamics is shown for the heart valve made from a single cylindrical shape.
Figure 3:
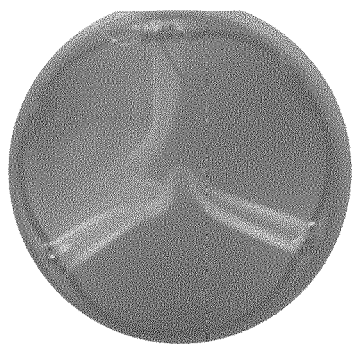
Figure 3:
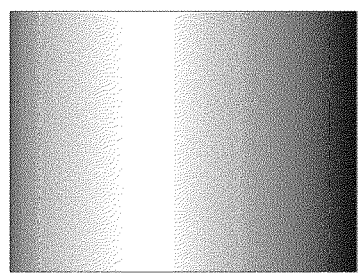
Figure 3:
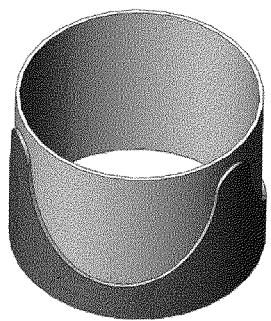
Figure 3:
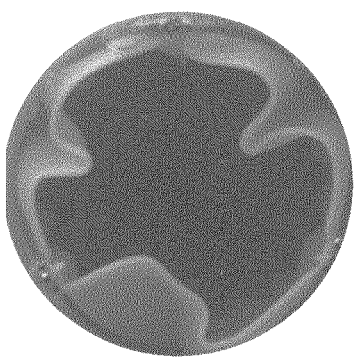
Figure 3:
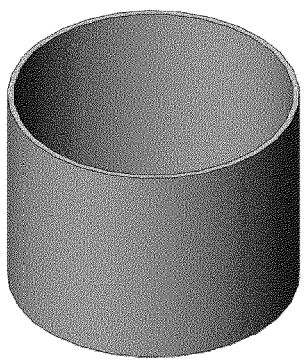

In one embodiment of the invention for producing the valve, a preform with a conical shape is produced (FIG. 1). When using this conically shaped preforms for producing leaflets it was found that mobility of the leaflets increased significantly. The preform could be produced by electrospinning on a conical mandrel. Alternatively, other techniques could be used which create thin membrane-like structures like 3D printing, dip coating, spray coating, molding and knitting techniques.

When using natural tissue for the leaflets, the material is normally thinner than artificial scaffolds. The use of natural tissue leads to better properties in terms of mobility. When using artificial scaffolds, the materials are thicker and show problems when folding during opening and closing of the valve.

Surprisingly, it was found by the inventors that a conical shape would lead to better folding during the closing of the heart valve. Thereby the mobility of the heart valve is significantly improved.

Embodiments of using conically-shaped preforms to produce conically-shaped scaffolds could have an overall length of the spun scaffold of between 20 to 300 mm in length. The overall length of the final scaffold device could be between 10 to 100 mm depending on the valve shape.

The maximum diameter of the scaffold device could be in the range of 10 to 40 mm, preferred between 16 to 28 mm. Much bigger diameters would have a negative effect on fiber alignment especially in the conical areas.

Operational limitations lead to a max diameter of 100 mm. Through experimentation for the purposes of this invention, the inventor has developed significant experience in a range of 16 to 28 mm, anything outside that should be possible in theory, but may have an effect on fiber alignment.

To create the conical design the angle is more than 0.5° and it will have not more than 12.5° maximum. Preferred is an angle between 1° and 6°. The design of the preform and obviously the resulting scaffold could have an overall conical shape within the dimensions described above.

Figure 4:
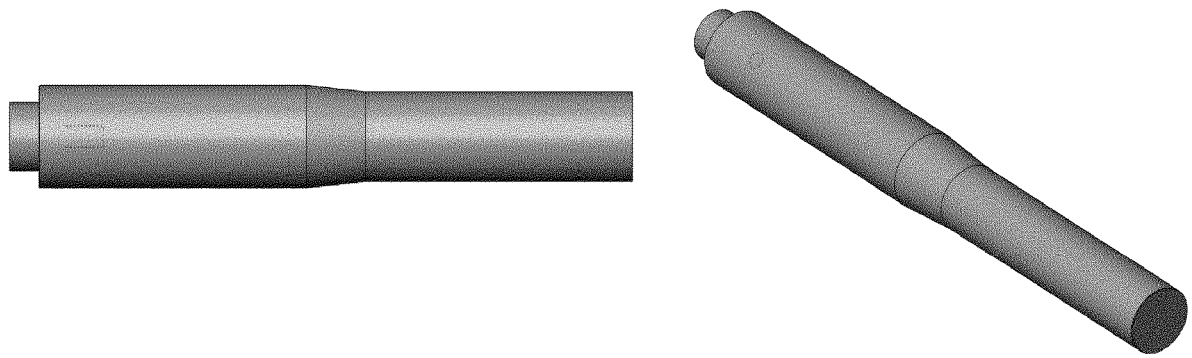
FIG. 4 shows according to an exemplary embodiment of the invention alternative mandrel with a conical shaped section and a cylindrical shaped section (top) for forming a single cylindrical and conical shaped electrospun scaffold (middle) by electrospinning polymers onto both the conical shaped section and the cylindrical shaped section of the mandrel (top). It is noted that the single cylindrical and conical shaped electrospun scaffold remains in one single piece after the plurality leaflets have been shaped.
Figure 4:

A second embodiment of the design could have a cylindrical lower portion as well as a conical upper portion (FIG. 4). Here the target base has a diameter of 24 mm which tapers to a 22 mm diameter over a length of 15 mm, creating a tapering angle is ~3.5°. By having cylindrical sections at both ends during electrospinning, the electric field gets more stable, which is beneficial for the predictability of the scaffolds and the correct alignments of the fibers.

Figure 5:
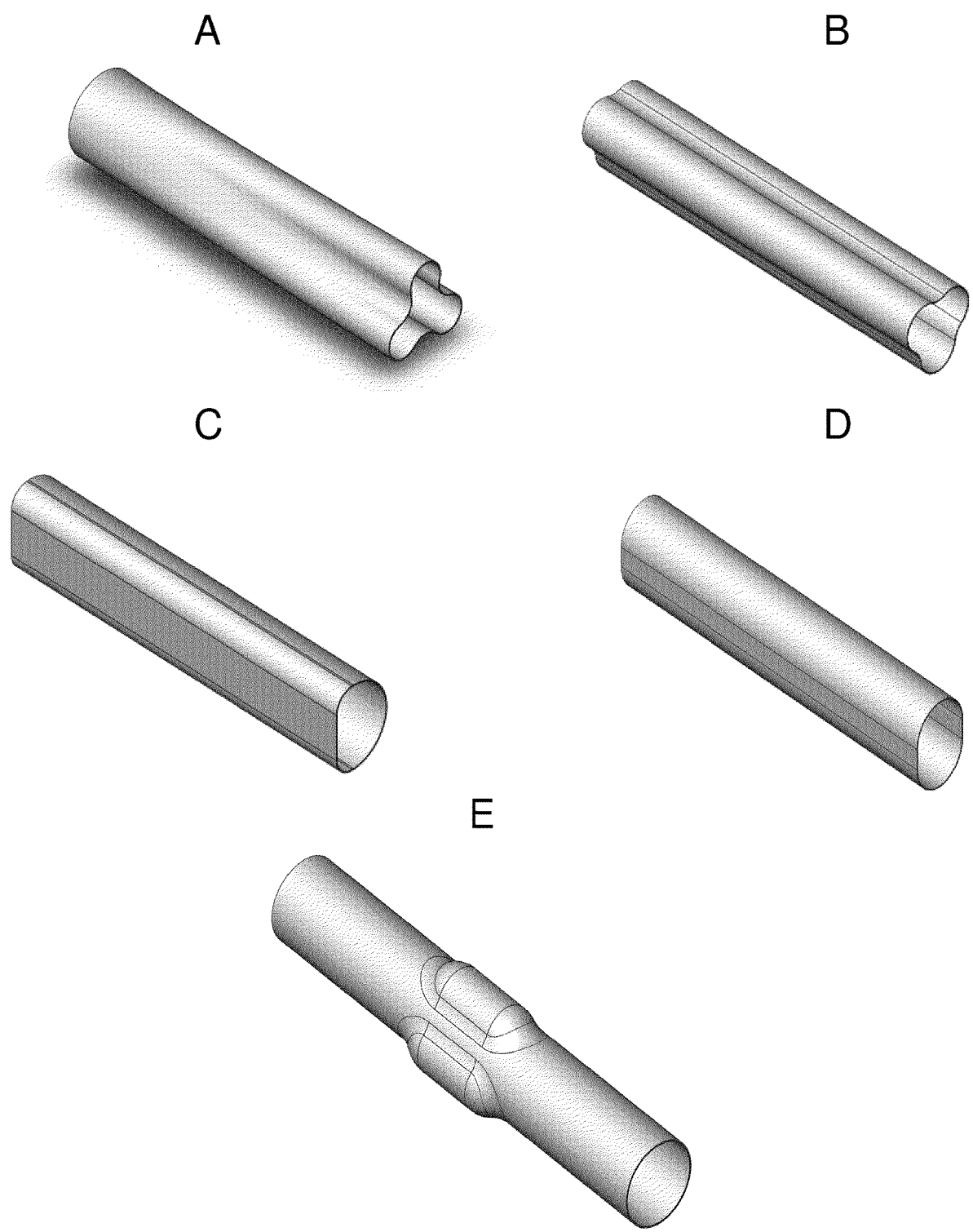
FIG. 5 shows according to exemplary embodiments (A-E) of the invention scaffolds produced from irregular or complex shaped mandrels (not shown) as variations to the examples of FIGS. 1-4. The complex shaped mandrels could have a cylindrical shaped mandrel with a surface that further defines one or more three-dimensional shapes (bulges or lobes). Still, like the examples of FIGS. 1-4, a single complex shaped electrospun scaffold is formed by electrospinning polymers onto the complex shaped mandrel including the one or more three-dimensional shapes. The single complex shaped electrospun scaffold is shaped into the heart valve shaped with the plurality of leaflets. It is noted that the single complex shaped electrospun scaffold remains in one single piece after the plurality leaflets have been shaped.

The design could have a circular radial shape as well as an irregular radial shape. For a tricuspid valve a tri-shaped geometry could be produced, for a mitral valve a geometry with two bellies or an oval shape could be applied. A selection of possible irregular shapes is shown in FIG. 5. The radius can vary along the axis.

Example A—The irregular radial shape can be combined with an irregular axial shape. This has the additional benefit that the required beneficial effect can be localized to the area of the scaffold that is to be used for leaflets. Other sections of the valve scaffold material can be left unaffected. It could be used in tricuspid heart valves.

Example B—Scaffolds with an irregular radial shape can have beneficial effects on the material behavior of the final heart valve. The preform used above allows for a modification of the stresses occurring within the leaflets. Depending on the changes, this can lead to improvements in durability as the peak stresses leading to failures can be reduces. Additionally, the shaping allows for the creation of a bias for the valve to be normally open or normally closed. This effect can be used to improve the mobility of the valve. This shape can be used to for flipping inside-out to achieve a more pronounced effect. Without flipping inside-out the effect can also be achieved. It could be used in tricuspid heart valves.

Examples C-D—The same beneficial effects as the other examples can be applied towards bicuspid heart valves. For bicuspid valves, the mandrel to create the scaffold is not using a three lobed shape, but a two-lobed or D-shape in order to mimic the native anatomy more closely.

Example E—By increasing the complexity of the shape of the mandrel, the shape of the scaffold can be further optimized to achieve a more localized beneficial effect for the leaflets of the final heart valve. It could be used in tricuspid heart valves.

Measurement of Mobility

Figure 6:
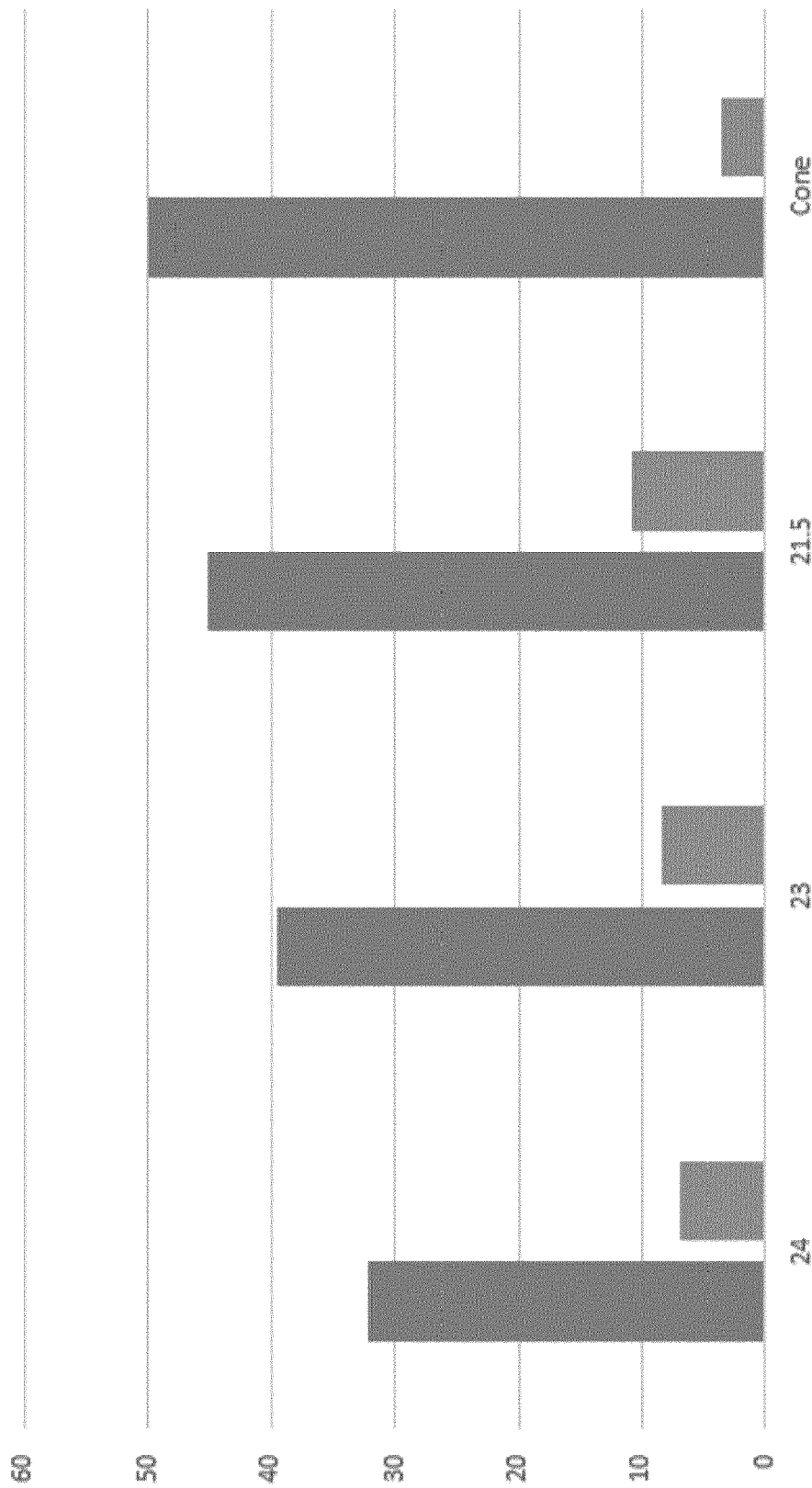
FIG. 6 shows according to an exemplary embodiment of the invention improvement of leaflet mobility of a heart valve (left bars in each set of bars) and improvement of closing of a heart valve (right bars in each set of bars). Numbers of vertical axis are in percentages.

With respect to FIG. 6, four different designs were tested with regard to their mobility characteristics. Three designs are tubular shapes with different diameters (24 mm, 23 mm, 21.5 mm) and one conical design ("Cone") with a diameter between 21.5 and 24 mm. The length of the tested scaffolds was 34 mm in order to produce a valve with a length of 30 mm.

"Mobility quotient" is based on the duration of opening multiplied by the extent of opening. Based on the average of all three leaflets the quotient scores higher with better mobility—the theoretical perfect valve would score 100%. The conical design performed best in the test and is therefore preferred.

Measurement of Valve Closing

With respect to FIG. 6, four different designs were tested with regard to their closing characteristics. Three designs are tubular shapes with different diameters (24 mm, 23 mm, 21.5 mm) and one conical design ("Cone") with a diameter between 21.5 and 24 mm. The length of the tested scaffolds was 34 mm in order to produce a valve with a length of 30 mm.

"STD between leaflets" is the standard deviation of score per leaflet. The value scores lower for better characteristics in closing and higher for asymmetric opening and closing of the leaflets with respect to each other. The conical valve has by far the lowest value and is therefore showing best characteristics with regard to perfect closing of the valve.

The electrospun material referenced in this document may comprise the ureido-pyrimidinone (UPy) quadruple hydrogen-bonding motif (pioneered by Sijbesma (1997), Science 278, 1601-1604) and a polymer backbone, for example selected from the group of biodegradable polyesters, polyurethanes, polycarbonates, poly(orthoesters), polyphosphoesters, polyanhydrides, polyphosphazenes, polyhydroxylkanoates, polyvinylalcohol, polypropylenefumarate. Examples of polyesters are polycaprolactone, poly(L-lactide), poly(DL-lactide), poly(valerolactone), polyglycolide, polydioxanone, and their copolyesters. Examples of polycarbonates are poly(trimethylenecarbonate), poly(dimethyltrimethylenecarbonate), poly(hexamethylene carbonate).

The same result may be obtained with alternative, non-supramolecular polymers, if properties are carefully selected and material processed to ensure required surface characteristics. These polymers may comprise biodegradable or non-biodegradable polyesters, polyurethanes, polycarbonates, poly(orthoesters), polyphosphoesters, polyanhydrides, polyphosphazenes, polyhydroxyalkanoates, polyvinylalcohol, polypropylenefumarate. Examples of polyesters are polycaprolactone, poly(L-lactide), poly(DL-lactide), poly (valerolactone), polyglycolide, polydioxanone, and their copolyesters. Examples of polycarbonates are poly(trimethylenecarbonate), poly(dimethyltrimethylenecarbonate), poly(hexamethylene carbonate).

Endogenous Tissue Restoration (ETR)

In one embodiment, the resulting device is made from bioabsorbable and/or biodegradable polymers which form a porous polymer network. The pores are of sufficient size allowing, upon implantation of the device, for a patient's own cells and nutrients to growth into the pores of the device to make autologous tissue tissue and eventually replace the implanted device. The key aspect of this concept is that the device is fully functional, like for example as a heat valve, upon implantation, and given that sufficiently porous structure the device allows cells and nutrients to infiltrate and permeate and replace the material with patient's own tissue.

Electrospinning Method

The technique of electrospinning is known in the art. The reader is referred to, for example WO2010041944, in which the preparation of an article by electro-spinning of polymer microfibers is disclosed.

Method of Shaping the Single Shape

In the method of shaping the single shape into e.g. a heart valve, the single shape could be molded around a semi-rigid valve support frame. The single shape is either formed/folded around that support frame or positioned inside the support frame. Sutures could be used to assemble the shape onto the frame. Alternatively, the frame could be laminated between 2 layers of the valve shape. Instead of using a semi-rigid frame, one could also use a self-expandable or balloon-expandable frame to create a transcatheter valve. The top (leaflet free edge) of the shape would typically be cut to optimize the shape of the free edge for coaptation and stress distribution, while the bottom (base) of the shape is cut to conform with the base (annular ring) of the support frame.

Method of Flipping of the Single Shaped Electrospun Scaffold

In a further embodiment, the single shaped electrospun scaffolds described herein and as part of the shaping process could include a further step, which is the step of flipping the single shaped electrospun scaffold. Once the scaffold is electrospun and removed from the mandrel, the scaffold is flipped inside-out resulting in the inner surface of the scaffold becoming the outer surface of the inside-out flipped scaffold, and the outer surface of the formed scaffold becoming the inner surface of the inside-out flipped scaffold.

At least part of the inside-out flipped scaffold forms the device such as e.g. an artificial heart valve.

What is claimed is:

1. A method of electrospinning a heart valve having a plurality of leaflets, comprising:
   (a) having a conical shaped mandrel with opposite ends both being circular shaped, wherein the conical shaped mandrel has a linear slope angle ranging from 1 to 12.5 degrees, wherein the linear slope is defined between the opposite ends of the conical shaped mandrel;
   (b) forming a single conically shaped electrospun scaffold by electrospinning polymers onto the conical shaped mandrel; and
   (c) shaping the single conically shaped electrospun scaffold into the heart valve shaped with the plurality of leaflets, wherein the single conically shaped electrospun scaffold remains in one single piece while shaping the plurality leaflets.

2. The method as set forth in claim 1, wherein the polymers are bioabsorbable polymers or biodegradable polymers, which upon implantation are replaced by new autologous tissue.

3. The method as set forth in claim 1, wherein the plurality is two or three thereby having a heart valve with respectively two or three leaflets.

4. The method as set forth in claim 1, wherein the conical shaped mandrel has a diameter ranging from 16 mm to 28 mm.

5. A method of electrospinning a heart valve having a plurality of leaflets, comprising:
   (a) having a mandrel with a conical shaped section with opposite ends both being circular shaped and a cylindrical shaped section with opposite ends both being circular shaped, wherein the conical shaped section has a linear slope angle ranging from 1 to 12.5 degrees, wherein the linear slope is defined between the opposite ends of the conical shaped section;
   (b) forming a single cylindrical and conical shaped electrospun scaffold by electrospinning polymers onto both the conical shaped section and the cylindrical shaped section of the mandrel; and
   (c) shaping the single cylindrical and conical shaped electrospun scaffold into the heart valve shaped with the plurality of leaflets, wherein the single cylindrical and conical shaped electrospun scaffold remains in one single piece while shaping the plurality leaflets.

6. The method as set forth in claim 5, wherein the polymers are bioabsorbable or biodegradable polymers, which upon implantation are replaced by new autologous tissue.

7. The method as set forth in claim 5, wherein the plurality is two or three thereby having a heart valve with respectively two or three leaflets.

8. The method as set forth in claim 5, wherein the conical shaped section of the mandrel has a diameter ranging from 16 mm to 28 mm.

9. A method of electrospinning a heart valve having a plurality of leaflets, comprising:
   (a) having a complex shaped mandrel, wherein the complex shaped mandrel with a complex surface comprises a conical shaped portion with opposite ends of the conical shaped portion both being circular shaped, wherein the complex surface further comprises one or more three-dimensional shapes, wherein the conical shaped portion has a linear slope angle ranging from 1 to 12.5 degrees, wherein the linear slope is defined between the opposite ends of the conical shaped portion;
   (b) forming a single complex shaped electrospun scaffold by electrospinning polymers onto the complex shaped mandrel including the one or more three-dimensional shapes; and
   (c) shaping the single complex shaped electrospun scaffold into the heart valve shaped with the plurality of leaflets, wherein the single complex shaped electrospun scaffold remains in one single piece while shaping the plurality leaflets.

10. The method as set forth in claim 9, wherein the polymers are bioabsorbable or biodegradable polymers, which upon implantation are replaced by new autologous tissue.

11. The method as set forth in claim 9, wherein the plurality is two or three thereby having a heart valve with respectively two or three leaflets.

12. The method as set forth in claim 9, wherein the conical shaped portion of the mandrel has a diameter ranging from 16 mm to 28 mm.

13. The method as set forth in claim 9, wherein the one or more three-dimensional shapes are one or more bulges to create one or more local bulges in the plurality of leaflets.

14. The method as set forth in claim 9, wherein the one or more three- dimensional shapes are one or more lobes to create one or more local lobes in the plurality of leaflets.

* * * * *